(12) United States Patent
He et al.

(10) Patent No.: US 11,893,831 B2
(45) Date of Patent: Feb. 6, 2024

(54) IDENTITY INFORMATION PROCESSING METHOD AND DEVICE BASED ON FUNDUS IMAGE

(71) Applicant: SHANGHAI EAGLEVISION MEDICAL TECHNOLOGY CO., LTD., Shanghai (CN)

(72) Inventors: Andre Wang He, Shanghai (CN); Jianhao Xiong, Shanghai (CN); Meng Fu, Shanghai (CN); Xiaopei Zhu, Shanghai (CN); Xin Zhao, Shanghai (CN); Chao He, Shanghai (CN); Dalei Zhang, Shanghai (CN)

( * ) Notice: Subject to any disclaimer, the term of this patent is extended or adjusted under 35 U.S.C. 154(b) by 100 days.

(21) Appl. No.: 17/619,875

(22) PCT Filed: Apr. 8, 2020

(86) PCT No.: PCT/CN2020/083625
§ 371 (c)(1),
(2) Date: Dec. 16, 2021

(87) PCT Pub. No.: WO2020/258981
PCT Pub. Date: Dec. 30, 2020

(65) Prior Publication Data
US 2022/0358791 A1 Nov. 10, 2022

(30) Foreign Application Priority Data
Jun. 28, 2019 (CN) .......................... 201910578335.4

(51) Int. Cl.
*G06V 40/18* (2022.01)
*G06V 10/82* (2022.01)
*G06V 40/50* (2022.01)

(52) U.S. Cl.
CPC ............ *G06V 40/193* (2022.01); *G06V 10/82* (2022.01); *G06V 40/197* (2022.01); *G06V 40/50* (2022.01)

(58) Field of Classification Search
None
See application file for complete search history.

(56) References Cited

U.S. PATENT DOCUMENTS

| 2015/0071504 A1* | 3/2015 | Cheswick | G06V 40/173 |
| | | | 382/118 |
| 2015/0265144 A1* | 9/2015 | Burlina | A61B 3/0025 |
| | | | 351/246 |

(Continued)

FOREIGN PATENT DOCUMENTS

| CN | 102254189 A | 11/2011 |
| CN | 102496007 A | 6/2012 |

(Continued)

OTHER PUBLICATIONS

Xiaodong Li, "Visual Navigation in Unmanned Air Vehicles With Simultaneous Location and Mapping (SLAM), " PhD Thesis, Cranfield University, Jan. 2014 (Year: 2014).*

(Continued)

*Primary Examiner* — Soo Shin
(74) *Attorney, Agent, or Firm* — Zhong Law LLC

(57) ABSTRACT

The present disclosure provides a method and device to process identity information based on a fundus image. An identity information comparison method includes: recognizing a fundus image by using a neural network to obtain a multi-dimensional feature vector representing the identity of a user; comparing the obtained multi-dimensional feature vector with each multi-dimensional feature vector stored in a database; and determining, according to a comparison result, whether there is a matching between the currently (Continued)

obtained multi-dimensional feature vector and a multi-dimensional feature vector pre-stored in the database.

12 Claims, 3 Drawing Sheets

(56) References Cited

U.S. PATENT DOCUMENTS

| | | | |
|---|---|---|---|
| 2018/0018451 A1 | 1/2018 | Spizhevoy et al. | |
| 2018/0140180 A1* | 5/2018 | Coleman | G06V 40/197 |
| 2019/0130566 A1* | 5/2019 | Niemeijer | G06F 18/2148 |
| 2020/0405148 A1* | 12/2020 | Tran | A61B 3/0016 |

FOREIGN PATENT DOCUMENTS

| | | | |
|---|---|---|---|
| CN | 103605962 | A | 2/2014 |
| CN | 106022317 | A | 10/2016 |
| CN | 106228142 | A | 12/2016 |
| CN | 107247940 | A | 10/2017 |
| CN | 109101913 | A | 12/2018 |
| CN | 109390053 | A | 2/2019 |
| CN | 109614613 | A | 4/2019 |
| CN | 109902665 | A | 6/2019 |
| CN | 110263755 | A | 9/2019 |
| CN | 110414423 | A | 11/2019 |
| CN | 110427804 | A | 11/2019 |
| IN | 108229539 | A | 6/2018 |

OTHER PUBLICATIONS

Waheed et al., "Person identification using vascular and non-vascular retinal features," Computers and Electrical Engineering 53 (2016) 359-371 (Year: 2016).*

Oinonen, et al., "Identity Verification Based on Vessel Matching From Fundus Images," Proceedings of 2010 IEEE 17th International Conference on Image Processing (Year: 2010).*

International Search Report and Written Opinion Application No. PCT/CN2020/083625, dated Jun. 30, 2020, 19 pages.

EPO Search report issued for EP application No. 20833250.2.

Laibacher Tim et al: "M2U-Net: Effective and Efficient Retinal Vessel Segmentation for Real-World Applications", 2019 IEEE/CVF Conference on Computer Vision and Pattern Recognition Workshops (CVPRW), Jun. 16, 2019 (Jun. 16, 2019), pp. 115-124, XP033746923, IEEE , Los Alamitos, CA, USA * abstract *.

Sadikoglu Fahreddin et al: "Biometric Retina Identification Based on Neural Network", Procedia Computer Science, vol ~ 102, Oct. 25, 2016 (Oct. 25, 2016), pp. 26-33, XP029785152, Elsevier, Amsterdam, NL.

Waheed Zahra et al: "Person identification using vascular and non-vascular retinal features", Computers & Electrical Engineering, vol. 53, Apr. 7, 2016 (Apr. 7, 2016), 359-371, XP029760651, Pergamon Press, GB * Section 1. * * Section 3 and sub-sections. *.

* cited by examiner

IDENTITY INFORMATION PROCESSING METHOD AND DEVICE BASED ON FUNDUS IMAGE

CROSS-REFERENCE TO RELATED APPLICATIONS

This application is the U.S. national stage of PCT/CN2020/083625 filed Apr. 8, 2020, which claims priority benefit to Chinese Patent Application No. 201910578335.4 filed Jun. 28, 2019. The contents of the above-mentioned applications are hereby incorporated by reference in their entireties.

TECHNICAL FIELD

The present disclosure relates to the field of image information processing, and in particular to an identity information processing method and device based on a fundus image.

BACKGROUND

A fundus image (also referred to as a retinal image) captured using a fundus camera can show human tissues such as the macula, optic disc, and blood vessels. The fundus image is highly unique because the vascular orientation, bifurcations, and the shape of the optic disc are different from person to person, but the fundus image of a particular person does not change significantly with age.

Current technologies use fundus images to identify identity information. Accordingly a database of identity information based on fundus images needs to be established. An important question is what information to store during the establishment of a database. Most of the literatures, similar to a fingerprint or facial recognition technologies, identify and extract information about shape features of some key points using computer vision methods. Such information is stored in the database for subsequent comparison. However, the analysis of a fundus image is very different from that of a fingerprint image and a face image, and it is very difficult to determine key points and to find corresponding key points between two fundus images, resulting in poor usability. Therefore, in some existing technologies, a fundus image of a user is directly stored. That is, the fundus image is directly used as identity information of the user.

In a database with a large amount of identity information of users, when the identity information of a current user is obtained, the first step is to determine whether the identity information of the user is already stored in the database. If fundus images are stored in the database, all the fundus images already stored in the database need to be separately compared with the current fundus image. This approach is very inefficient.

SUMMARY

In view of this, an implementation of the present disclosure provides an identity information comparison method based on a fundus image, including:
  recognizing a fundus image by using a neural network to obtain a multi-dimensional feature vector representing the identity of a user;
  comparing the obtained multi-dimensional feature vector with each multi-dimensional feature vector pre-stored in a database; and
  determining, according to a comparison result, whether there is a matching between the currently obtained multi-dimensional feature vector and a multi-dimensional feature vector matching pre-stored in the database.

Optionally, the neural network is trained with triple sample data. The triple sample data includes a first fundus image sample, a second fundus image sample, and a third fundus image sample. The second fundus image sample and the first fundus image sample are fundus images of the same person, and the third fundus image sample and the first fundus image sample are fundus images of different people.

Optionally, in a process of training the neural network, the neural network separately extracts multi-dimensional feature vectors of the first fundus image sample, the second fundus image sample, and the third fundus image sample; calculates a first distance between the second fundus image sample and the first fundus image sample, and a second distance between the third fundus image sample and the first fundus image sample according to the three extracted multi-dimensional feature vectors; obtains a loss value according to the first distance and the second distance; and adjusts parameters of the neural network according to the loss value.

Optionally, the adjusting parameters of the neural network according to the loss value includes:
  feeding back the loss value to the neural network, to enable the neural network to adjust the parameters according to the loss value to decrease the first distance and increase the second distance until the first distance is smaller than the second distance by a preset value.

Optionally, the determining, according to a comparison result, whether there is a matching between the currently obtained multi-dimensional feature vector and a multi-dimensional feature vector pre-stored in the database includes:
  calculating a distance between each pre-stored multi-dimensional feature vector and the currently obtained multi-dimensional feature vector; and
  determining, according to the distance, whether each pre-stored multi-dimensional feature vector matches the currently obtained multi-dimensional feature vector.

Optionally, the fundus image includes a left-eye fundus image and a right-eye fundus image. The database is configured to store user data. Each group of user data includes a first pre-stored multi-dimensional feature vector corresponding to a left eye and a second pre-stored multi-dimensional feature vector corresponding to a right eye. The multi-dimensional feature vector includes a first multi-dimensional feature vector corresponding to the left-eye fundus image and a second multi-dimensional feature vector corresponding to the right-eye fundus image.

Optionally, the fundus image includes a left-eye fundus image and a right-eye fundus image, the database is configured to store user data, and each group of user data includes one pre-stored multi-dimensional feature vector.

The obtaining a multi-dimensional feature vector representing the identity of a user includes:
  acquiring the first multi-dimensional feature vector corresponding to the left-eye fundus image and the second multi-dimensional feature vector corresponding to the right-eye fundus image that are output by the neural network; and
  combining the first multi-dimensional feature vector and the second multi-dimensional feature vector to obtain the multi-dimensional feature vector representing the identity of the user.

Optionally, the fundus image is a left-eye fundus image or a right-eye fundus image, the database is configured to store user data, and each group of user data includes a first pre-stored multi-dimensional feature vector corresponding to a left eye or a second pre-stored multi-dimensional feature vector corresponding to a right eye.

The present disclosure further provides an identity verification method based on a fundus image, including:
acquiring a fundus image of a user; and
determining, by using the foregoing identity information comparison method based on a fundus image, whether there is a matching between a multi-dimensional feature vector of the fundus image and a multi-dimensional feature vector pre-stored in a database, to complete verification of the identity of the user.

The present disclosure further provides an identity information storage method based on a fundus image, including:
acquiring a fundus image of a user; and
determining, by using the foregoing identity information comparison method based on a fundus image, whether there is a matching between a multi-dimensional feature vector of the fundus image and a multi-dimensional feature vector pre-stored in a database; and
when there is no matching between a currently obtained multi-dimensional feature vector and a multi-dimensional feature vector pre-stored in the database, storing the currently obtained multi-dimensional feature vector in the database as identity information of the user.

The present disclosure further provides a method for training a fundus image recognition model, including:
acquiring training data, where the training data includes a first fundus image sample, a second fundus image sample, and a third fundus image sample, the second fundus image sample and the first fundus image sample are fundus images of the same person, and the third fundus image sample and the first fundus image sample are fundus images of different people;
recognizing the first fundus image sample, the second fundus image sample, and the third fundus image sample by using a fundus image recognition model to obtain a loss value; and
adjusting parameters of the fundus image recognition model according to the loss value.

Optionally, the recognizing the first fundus image sample, the second fundus image sample, and the third fundus image sample by using a fundus image recognition model to obtain a loss value includes:
calculating a first distance between the second fundus image sample and the first fundus image sample;
calculating a second distance between the third fundus image sample and the first fundus image sample; and
obtaining the loss value according to the first distance and the second distance.

Optionally, the adjusting parameters of the fundus image recognition model according to the loss value includes:
feeding back the loss value to the fundus image recognition model; and
adjusting the parameters according to the loss value to decrease the first distance and increase the second distance, until the first distance is smaller than the second distance by a preset value.

Correspondingly, an implementation of the present disclosure further provides a device for an identity information comparison based on a fundus image, the device including: at least one processor, and a memory communicatively connected to the at least one processor, where the memory stores an instruction executable by one processor, which when executed by the at least one processor, causes the at least one processor to carry out the foregoing identity information comparison method based on a fundus image.

Correspondingly, an implementation of the present disclosure further provides a device for identity verification based on a fundus image, the device including: at least one processor, and a memory communicatively connected to the at least one processor, where the memory stores an instruction executable by one processor, which when executed by the at least one processor, causes the at least one processor to carry out the foregoing identity verification method based on a fundus image.

Correspondingly, an implementation of the present disclosure further provides a device for an identity information storage based on a fundus image, the device including: at least one processor, and a memory communicatively connected to the at least one processor, where the memory stores an instruction executable by one processor, which when executed by the at least one processor, causes the at least one processor to carry out the foregoing identity information storage method based on a fundus image.

Correspondingly, an implementation of the present disclosure further provides a device for training a fundus image recognition model, the device including: at least one processor, and a memory communicatively connected to the at least one processor, where the memory stores an instruction executable by one processor, which when executed by the at least one processor, causes the at least one processor to carry out the foregoing method for training a fundus image recognition model.

According to the method and device of the identity information comparison based on a fundus image provided in the present disclosure, a neural network is first used to convert a fundus image of a user into a multi-dimensional feature vector representing the identity of the user, and then abstract feature information related to personal features of the user is extracted by using characteristics of the neural network. During comparison, implementations of the disclosure may determine by comparing multi-dimensional feature vectors whether there is data matching with the current user in a database. In this implementation, the database does not need to store a fundus image. It is also unnecessary to recognize pre-stored fundus images repeatedly every time a new fundus image is obtained, so that the efficiency of operation of an identity information comparison can be improved.

A neural network provided according to the implementation of the present disclosure is trained with triple training data and a corresponding loss function, so that a distance between feature vectors extracted by the neural network from different fundus images of the same eye can be decreased, and a distance between feature vectors extracted from fundus images of different eyes can be increased during the training process. After training, distances between feature vectors repeatedly extracted by the neural network from the same fundus image are small enough, and distances to feature vectors of other fundus images are large enough, that is, the information has particular uniqueness, so that feature vectors extracted by the neural network from fundus images can be used as identity information of a user.

BRIEF DESCRIPTION OF THE DRAWINGS

To describe the technical schemes in specific embodiments of the present disclosure or the existing technology more clearly, the following briefly introduces the accompanying drawings required for describing the specific embodiments or the existing technology. Apparently, the accompanying drawings in the following description show some embodiments of the present disclosure, and a person having ordinary skills in the art may still derive other drawings from these accompanying drawings without creative efforts.

DETAILED DESCRIPTION

The following clearly and completely describes the technical schemes of the present disclosure with reference to the accompanying drawings. Apparently, the described embodiments are merely some rather than all of the embodiments of the present disclosure. All other embodiments obtained by a person having ordinary skills in the art based on the embodiments of the present disclosure without creative efforts shall fall within the protection scope of the present disclosure.

In addition, the technical features involved in different embodiments of the present disclosure described below can be combined with each other as long as they do not constitute a conflict between them.

Figure 1:
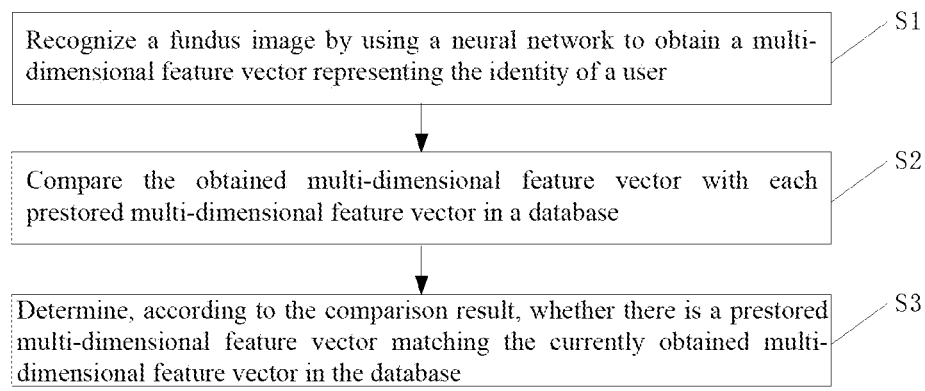
FIG. 1 is a flowchart of an identity information comparison method according to an embodiment of the present disclosure.

Embodiments of the present disclosure provide an identity information storage method based on a fundus image. The method may be performed by an electronic device such as a computer or a server. As shown in FIG. 1, the method includes the following steps S1 to S3.

At step S1, a fundus image is recognized by a neural network to obtain a multi-dimensional feature vector representing the identity of a user. The neural network extracts feature information during recognition of an image. For different tasks, the neural network focuses on different content, and different feature information is extracted. For example, during the execution of a classification task, the neural network extracts corresponding feature information (usually a multi-dimensional feature vector) according to a category of a fundus image, and then performs classification according to the feature information.

In this embodiment, the neural network used is configured to extract the multi-dimensional feature vector representing the identity of a user, rather than to perform a classification task or an image segmentation task. For different people (users), multi-dimensional feature vectors extracted by the neural network from fundus images of people should be different. For the same eye of the same person, during repeated recognition, multi-dimensional feature vectors extracted at different times should be the same (or approximately the same or similar). The neural network in this application may be a deep convolutional neural network (CNN), and extracted multi-dimensional feature vectors can be normalized by setting an appropriate loss function and using a back propagation (BP) algorithm. Then, a trained CNN model can be used to extract feature vectors, which are usually high-dimensionality vectors, from a fundus image.

To enable the neural network to extract expected content, the neural network should be trained beforehand. There are many training methods, and different training data are used for different training methods. Details are described below in detail.

At step S2, the obtained multi-dimensional feature vector is compared with each multi-dimensional feature vector pre-stored in a database. According to a configuration position of the database, the database may be categorized into a database configured based on a graphics processing unit (GPU) and a database configured based on a central processing unit (CPU). A multi-dimensional feature vector pre-stored in the database may alternatively be the multi-dimensional feature vector extracted by the neural network in step S1 from another fundus image.

There are many ways to compare two feature vectors. A comparison result is used to represent a similarity between the two feature vectors. A similarity between multi-dimensional vectors may be determined based on Euclidean distance, cosine similarity, normalized Euclidean distance, or the like. The Euclidean distance measures an absolute distance between points in a multi-dimensional space, which is preferred when data is very dense and continuous. Since the calculation is based on absolute values of features of different dimensions, Euclidean measurement needs to ensure that indicators of different dimensions are at the same scale level.

In some specific scenarios, Mahalanobis distance may be used. The Mahalanobis distance is a distance based on sample distribution. For example, for two populations of normal distribution with an average value of a and b, respectively but having different variances, the probability of which distribution a sample point A belongs to in a distribution space is higher determines that A belongs to this distribution.

Because different constraint distances are used to establish a feature space, different comparison methods should be adopted when comparing the results.

During practical application, multi-dimensional feature vectors extracted by the neural network from fundus images of the same person captured at different moments and in different environments are usually not identical. Therefore, using a distance calculation method to measure a similarity between two feature vectors has a certain fault tolerance, and the distance is preferably a Euclidean distance.

In another optional embodiment, it is also feasible to calculate an angle between each pre-stored multi-dimensional feature vector and the currently obtained multi-dimensional feature vector to measure a similarity therebetween.

At step S3, whether there is a matching between the currently obtained multi-dimensional feature vector and a multi-dimensional feature vector pre-stored in the database is determined according to a comparison result. Different comparison methods may result in different comparison results. For example, whether each pre-stored multi-dimensional feature vector matches the currently obtained multi-dimensional feature vector may be determined based on the distance or the angle.

Taking distance as an example, when the distance between the two feature vectors is less than a set threshold, it can be determined that the two feature vectors have a sufficiently high similarity, indicating that the two match each other.

According to an identity information comparison method based on a fundus image provided in the embodiments of the present disclosure, a neural network is first used to convert a fundus image of a user into a multi-dimensional feature vector used for representing the identity of the user, and then abstract feature information related to personal features of the user is extracted using characteristics of the neural network. During comparison, whether there is data matching the current user in a database can be determined by comparing multi-dimensional feature vectors. In this scheme, the database does not need to store fundus images. It is also unnecessary to recognize pre-stored fundus images repeatedly every time a new fundus image is obtained, thereby improving the efficiency of an identity information comparison operation.

This scheme may be used to process a fundus image of one eye of a user. That is, the fundus image recognized in step S1 is a left-eye fundus image or a right-eye fundus image. Correspondingly, feature vectors stored in the database are from fundus images of one eye.

This scheme may be extended to process fundus images of two eyes of a user. That is, the fundus images in step S1 include a left-eye fundus image and a right-eye fundus image. The two fundus images are separately recognized by the neural network, to obtain a first multi-dimensional feature vector corresponding to the left-eye fundus image and a second multi-dimensional feature vector corresponding to the right-eye fundus image. Correspondingly, each group of data stored in the database includes two pre-stored multi-dimensional feature vectors, which may be correspondingly compared in step S2.

When comparison is separately performed for two eyes, it is possible that a feature vector of one eye matches the data in the database whereas a feature vector of the other eye does not match the data in the database. Such a result is acceptable in some application scenarios, for example, during establishment or update of the database. However, such a result is not allowed in certain application scenarios, for example, during identity verification.

In a preferred embodiment, according to this scheme, fundus images of two eyes of a user are uniformly processed. Recognized fundus images include a left-eye fundus image and a right-eye fundus image. The fundus images of two eyes are separately recognized by using the neural network in step S1, and a first multi-dimensional feature vector corresponding to the left-eye fundus image and a second multi-dimensional feature vector corresponding to the right-eye fundus image are output. The two feature vectors are then combined, which may be performed in multiple ways. For example, two 1024-dimensional feature vectors may be connected into one 2048-dimensional feature vector.

Correspondingly, the pre-stored data in the database is a combined multi-dimensional feature vector, and is a result of combining two feature vectors in advance. During comparison in step S2, the currently combined dimensional feature vector is compared with a pre-stored multi-dimensional feature vector in the database, to further determine, according to a comparison result, whether there is matching data. In this embodiment, it only needs to perform one comparison to determine whether there are matching data of the two eyes.

Figure 2:
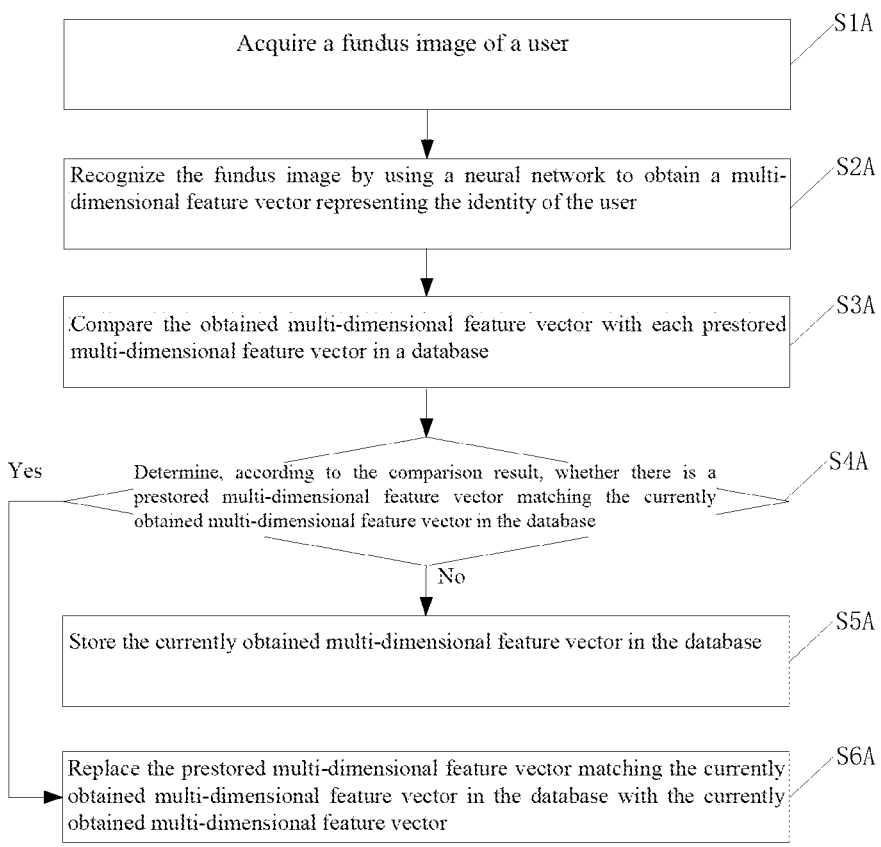
FIG. 2 is a flowchart of an identity information storage method according to an embodiment of the present disclosure.

An identity information storage method based on a fundus image is described below. The method uses the foregoing comparison embodiment to establish and manage an identity information database. As shown in FIG. 2, the method includes the following steps S1A to S6A.

At step S1A, a fundus image of a user is acquired. According to the foregoing introduction, the fundus image may be a fundus image of either or both eyes.

At step S2A, the fundus image is recognized using a neural network to obtain a multi-dimensional feature vector representing the identity of the user. Reference may be made to the foregoing step S1 for details, which will not be described herein.

At step S3A, the obtained multi-dimensional feature vector is compared with each multi-dimensional feature vector pre-stored in a database. Reference may be made to the foregoing step S2, which will not be described herein.

At step S4A, whether there is a matching between the currently obtained multi-dimensional feature vector and a multi-dimensional feature vector pre-stored in the database is determined according to a comparison result. When there is no pre-stored multi-dimensional feature vector matching the currently obtained multi-dimensional feature vector in the database, step S5A is performed, or otherwise step S6A is performed.

It needs to be noted that the database may initially be empty, and has no pre-stored multi-dimensional feature vector, thus there is no matching content. A plurality of pieces of data may be imported into the initial database in advance. The data uses individuals as basic modules. For example, each piece of user data includes the name of the user and a multi-dimensional feature vector of the user (which is obtained based on a fundus image of the user), and may additionally include personal information such as the gender, age, diopter of the user, and the like.

If it is determined after one-by-one comparison that there is no pre-stored multi-dimensional feature vector matching the multi-dimensional feature vector of the current user in the database, it indicates that identity information of the current user is not stored in the database; or otherwise it indicates that the identity information of the current user has been stored in the database.

At step S5A, the currently obtained multi-dimensional feature vector is stored in the database. Specifically, when a multi-dimensional feature vector is not found in an original database, the system may prompt whether it is necessary to add the currently obtained multi-dimensional feature vector to the original database as a new piece of data. If YES is chosen, a request to memory is sent, and after the request succeeds, the new piece of data is added to the original database. Further, the system may further prompt whether to continue to input related supplementary information, for example, personal information such as the gender, age, the diopter, and the like of the user. After the information is entered, the information and the corresponding multi-dimensional feature vectors are stored as related data items.

At step S6A, the pre-stored multi-dimensional feature vector matching the currently obtained multi-dimensional feature vector in the database is replaced with the currently obtained multi-dimensional feature vector. Specifically, when a multi-dimensional feature vector matching the current multi-dimensional feature vector is found in the database, the system may prompt whether it is necessary to overwrite existing data with the currently obtained multi-dimensional feature vector. If YES is chosen, overwriting is performed. This step is an optional operation. As an alternative, when a multi-dimensional feature vector matching the current multi-dimensional feature vector is found in the database, the system may only prompt that current user data already exists, and a replacement operation is not required.

According to the identity information storage method based on a fundus image provided in the embodiments of the present disclosure, a neural network is first used to convert a fundus image of a user into a multi-dimensional feature vector used for representing the identity of the user, and then abstract feature information related to personal features of the user is extracted using characteristics of the neural network. During storage, whether there is data matching the current user in a database can be determined by comparing multi-dimensional feature vectors, so as to store the multi-dimensional feature vector. In this scheme, the database does not need to store a fundus image. It is also not necessary to recognize an existing fundus image by using the neural network during the storage of every piece of identity information of the user, thereby improving the efficiency of storing identity information of users.

As exemplary description, each piece of information of the user in the database established according to the scheme may include the name of the user, a multi-dimensional feature vector (a first multi-dimensional feature vector of a left eye and/or a second multi-dimensional feature vector of a right eye or a combination of the two), the gender, age, diopter of the user, and the like. The multi-dimensional feature vector represents the identity information of the user.

A process of establishing and managing a database is described in the foregoing embodiments. Some changes may be further made on this basis to obtain an identity verification scheme. Specifically, according to the conclusion of step S4A, that is, whether the identity information of the current user is stored in the database, a corresponding identity determination operation can be performed. For example, at step S5A, it is determined that the current user is not a known user, and therefore the current user is not allowed to perform a subsequent operation; and at step S6A, it is determined that the current user is a known user, and therefore the current user is allowed to perform a subsequent operation. The subsequent operation may be unlocking or logging in an electronic device, or the like, to implement identity verification, authentication, or the like.

An embodiment of the present disclosure further provides a device of an identity information comparison based on a fundus image, the device including: at least one processor, and a memory communicatively connected to the at least one processor, where the memory stores an instruction executable by one processor, which when executed by the at least one processor, causes the at least one processor to carry out the foregoing identity information comparison method based on a fundus image.

An embodiment of the present disclosure further provides a device of an identity information storage based on a fundus image, including: at least one processor, and a memory communicatively connected to the at least one processor, where the memory stores an instruction executable by one processor, which when executed by the at least one processor, causes the at least one processor to carry out the foregoing identity information storage method based on a fundus image.

An embodiment of the present disclosure further provides a device of an identity verification based on a fundus image, the device including: at least one processor, and a memory communicatively connected to the at least one processor, where the memory stores an instruction executable by one processor, which when executed by the at least one processor, causes the at least one processor to carry out the foregoing identity verification method based on a fundus image.

How to obtain a model for generating a feature vector is described below with reference to FIG. 3 to FIG. 5 (the neural network in the foregoing embodiments). Aspects to extract features may include: providing an optimized intra-class distance, to make the intra-class distance smaller; and providing an optimized inter-class distance, to make the inter-class distance more distinguishable. The intra-class distance refers to a distance between sample points of each pattern in the same class; and the inter-class distance refers to a distance between different classes. To achieve this objective and extract better feature vectors, there are the following optional embodiments.

Figure 3:
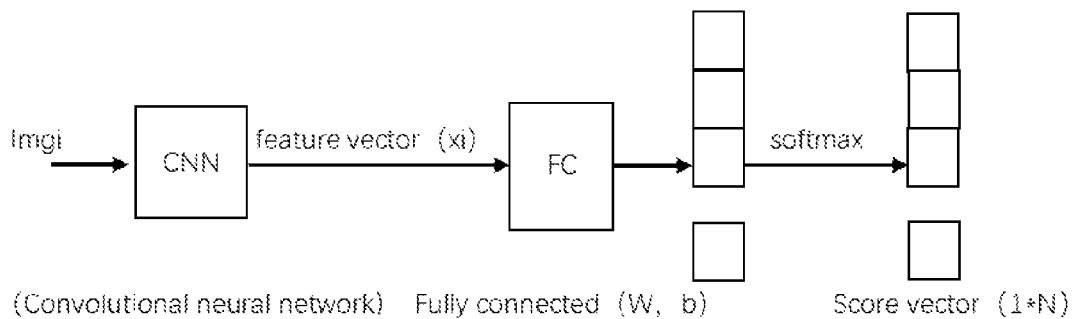
FIG. 3 is a schematic diagram of extracting identity information by using a neural network according to an embodiment of the present disclosure.

In a first optional embodiment, FIG. 3 shows a training framework of a softmax-based classification model. The framework of the classification model may be applied to training and extraction of identity features of fundus images, and on this basis, various auxiliary loss functions are provided to improve the characteristics of the identity features of the fundus images. A fundus image Imgi is fed into a deep CNN, to obtain a multi-dimensional feature vector $x_i$, and then passes through a fully connected layer and is processed by softmax, to obtain a score vector. The softmax loss function is shown as follows:

$$L_1 = -\frac{1}{N}\sum_{i=1}^{N} \log \frac{e^{w_{y_i}^T x_i + b_{y_i}}}{\sum_{k=1}^{n} e^{w_j^T x_i + b_j}},$$

where N is a batch size, n is a quantity of classes, $x_i$ denotes a feature vector of an $i^{th}$ fundus image of a batch, $y_i$ denotes an actual identity class (label) of the fundus image, $W_j$ denotes a vector of a $j^{th}$ column of a weight W of the fully connected layer, $$\frac{e^{w_{y_i}^T x_i + b_{y_i}}}{\sum_{k=1}^{n} e^{w_j^T x_i + b_j}} \in (0,1)$$

denotes a probability value that $x_i$ is predicted as the actual identity class of the fundus image, and $b_j$ is a bias value.

For example, a classification model (1, 2, 3) with n=3 is defined, where classes 1, 2, and 3 denote identity labels of three users. A score vector $s_i$ obtained for the fundus image Imgi is 0.1, 0.2, 0.7). It is determined that Imgi is a fundus image of a user with a label of 3. A contribution of Imgi to a loss value is $L_1$=−log(0.7)=0.3567. However, if the obtained score vector $s_i$ is 0.1, 0.5, 0.4). A contribution of Imgi to the loss value is $L_1$=−log(0.4)=0.9163. As shown, when a probability value that the model predicts the fundus image to be a correct identity class is large, the contribution to the loss value is small, or otherwise, the contribution to the loss value is large. A model trained using this loss function is used to extract a feature vector that can be used for correct classification.

It is highly crucial for an identity recognition task to minimize a difference between internal classes while ensuring that features of different classes are distinguishable. To achieve this, the following loss function may be set:

$$L = L_s + \lambda L_c = -\sum_{i=1}^{m} \log \frac{e^{w_{y_i}^T x_i + b_{y_i}}}{\sum_{k=1}^{n} e^{w_j^T x_i + b_j}} + \frac{\lambda}{2}\sum_{i=1}^{m} \|x_i - c_{y_i}\|_2^2.$$

Joint supervision of a softmax loss ($L_s$) and a center loss ($L_c$) is used to train the deep CNN to perform discriminative feature learning. The center loss can effectively characterize an intra-class change. A scalar $\lambda$ is used for striking a balance between $L_s$ and $L_c$. When $\lambda$ has different values, feature vectors have different distributions.

During training, a mini-batch of fundus images are input for each iteration, and m is the number of images input in each iteration. $x_i$ is a feature vector of an $i^{th}$ image in one batch. $y_i$ is an identity label of a user to which the fundus image $x_i$ belongs. $Cy_i \in Rd$ denotes the center of a feature vector of an identity classification label of a $y_i^{th}$ user, and d denotes a dimensionality of a feature vector. During training, with every iteration, the center $C_{yi}$ of a feature vector of each user label is updated. The center $C_{yi}$ is calculated by averaging features of corresponding classification labels. Next, to prevent a small number of incorrectly labeled samples from causing a major disturbance, a scalar $\alpha \in [0, 1]$ may be used to control a learning rate of the center. This scheme is distinguished in that the difference between internal classes can be reduced to the greatest extent while ensuring that features of different classes can be separated without complex recombination of training sets.

In a second optional embodiment, based on that joint supervision of a softmax loss ($L_s$) and a contrastive loss ($L_c$) is used to train the deep CNN to perform discriminative feature learning, not only the accuracy of classification is taken into consideration, but also an inter-class distance m (margin) is added to expand a decision boundary, so that positive samples have a higher similarity, and negative samples have a lower similarity.

Figure 4:
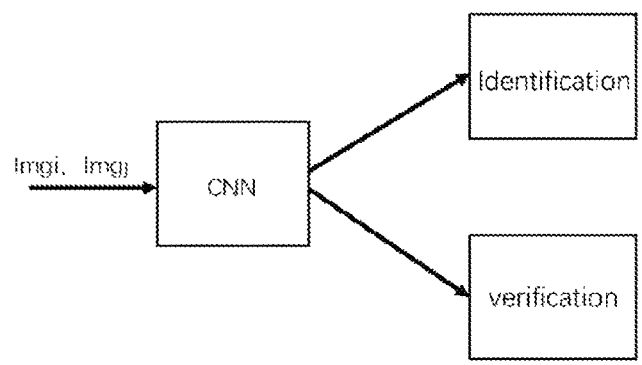
FIG. 4 is another schematic diagram of extracting identity information by using a neural network according to an embodiment of the present disclosure.

As shown in FIG. 4, a softmax layer with n channels is introduced after the structure of the deep CNN to obtain a recognition module for classifying an identity class of an input fundus image, where n is the number of user identity classes of the user, and is defined as an identification loss function:

$$\mathrm{Ident}(f, t, \theta_{id}) = -\Sigma_{i=1}^n p_i \log \hat{p}_i = -\log \hat{p}_t.$$

The foregoing formula is in fact a cross-entropy loss function, where f is a feature vector, t is a user identity class corresponding to the feature vector f, $\theta_{id}$ is a parameter of the softmax layer, and $p_i$ is a target probability distribution. For the user identity class t, $p_t = 1$, and for the remaining, $p_i = 0$. $\hat{p}_i$ is a predicted probability distribution. During training, since the network integrates the following verification loss function, which is in fact a contrastive loss, before training is performed using the following loss function, fundus images in a training set should be first paired to obtain image pairs, and it is labeled whether each image pair includes identity features of the same user. For feature vectors $(f_i, l_i)$ and $(f_1, l_j)$ of an input image pair, if $l_i = l_j$, it is labeled that the label is $y_{ij} = 0$; or otherwise, it is labeled that the label is $y_{ij} = 1$, as shown below:

$$\mathrm{Verif}(f_i, f_j, y_{ij}, \theta_{ve}) = \begin{cases} \frac{1}{2} \|f_i - f_j\|_2^2 & \text{if } y_{ij} = 1 \\ \frac{1}{2} \max(0, m - \|f_i - f_j\|_2)^2 & \text{if } y_{ij} = -1 \end{cases}.$$

During training, a fundus image pair is input into the deep CNN to obtain image features. Identification loss is separately calculated for the fundus image pair. That is, user identity classification is performed on two input fundus images, and verification is performed on the fundus image pair at the same time, to verify whether two input fundus images of the fundus image pair are the same. When the input fundus image pair have the same identity, that is, $y_{ij} = 0$, a feature vector of the fundus image pair is $(f_i, f_j)$, $\mathrm{Verif}(f_i, f_j, y_{i,j}, \theta_{ve}) = \frac{1}{2} \|f_i - f_j\|_2^2$. When the input fundus image pair do not have the same identity, that is, $y_{ij} = 1$, a feature vector of the fundus image pair is $(f_i, f_j)$, $\mathrm{Verif}(f_i, f_j, y_{ij}, \theta_{ve}) = \frac{1}{2} (\max(0, m - \|f_i - f_j\|_2))^2$, . . . , where L2 normalization is used for a similarity distance of the feature vector $(f_i, f_1)$. L1/L2 normalization or a cosine similarity is adopted, and m (margin) defines an inter-class margin, which acts on the loss value only when a distance in the image pair with different identities is within the distance m. This effectively restricts an inter-class distance, and therefore the inter-class distance is more distinguishable.

Figure 5:
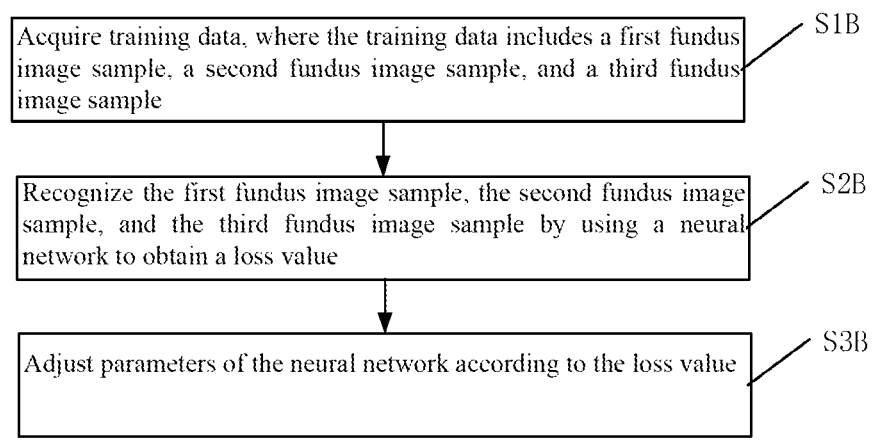
FIG. 5 is a flowchart of a neural network training method according to an embodiment of the present disclosure.

In a third optional embodiment, as shown in FIG. 5, embodiments of the present disclosure further provide a method for training a triple data-based model. The method includes the following steps S1B to S3B.

At step S1B, training data is acquired, where the training data includes a first fundus image sample, a second fundus image sample, and a third fundus image sample. The training data used in this embodiment is triple sample data. The second fundus image sample and the first fundus image sample are fundus images of the same eye of the same person. The third fundus image sample and the first fundus image sample are fundus images of different people.

In a specific embodiment, a data set is first prepared. As an example, the data set may include fundus images of n eyes. Each eye corresponds to m fundus images. That is, there are a total of n*m fundus images in the data set. To obtain training data, one fundus image is first randomly selected from the n*m fundus images, which is referred to as Anchor. Then another fundus image of the same eye as Anchor is selected, which is referred to as Positive (denoted as $x_{-p}$); and then one fundus image of an eye different from Anchor is selected, which is referred to as Negative (denoted as $x_{-n}$), so that a group of training data (Anchor, Positive, Negative) is obtained.

Before a neural network is trained by using the training data, a fundus image may be preprocessed first to allow the trained neural network to be more accurate during recognition of the fundus image. Specifically, each fundus image may first be cropped. Because a captured fundus image originally has a relatively large black background, the fundus images may first be trimmed to remove a large number of black pixels in the background, until all fundus images are cropped to the smallest rectangles that can contain the entire circular fundus.

In a specific embodiment, all fundus images may be cropped to a uniform format, for example, a size of 224*224 pixels. Fundus images used for model training and recognition may adopt a uniform format of 224*224 pixels and RGB color channels.

At step S2B, the first fundus image sample, the second fundus image sample, and the third fundus image sample are recognized by the neural network to obtain a loss value. A first distance between the second fundus image sample and the first fundus image sample, and a second distance between the third fundus image sample and the first fundus image sample are calculated according to a preset loss function, and a loss value is obtained according to the first distance and the second distance.

Specifically, the neural network separately extracts features of the foregoing three fundus images, to obtain three multi-dimensional feature vectors, which are respectively denoted as: $f(x_i^a)$, $f(x_i^p)$, and $f(x_i^n)$. Then a first distance between $f(x_i^a)$ and $f(x_i^p)$, and a second distance between $f(x_i^a)$ and $f(x_i^n)$ are calculated. The first distance and the second distance in this embodiment are Euclidean distances.

The loss value is calculated by using the first distance and the second distance, which may be performed by the following relational expression of the loss function.

$$\Sigma_i^N [\|f(x_i^a)-f(x_i^p)\|_2^2 - \|f(x_i^a)-f(x_i^n)\|_2^2 + a]_+,$$

where a denotes a preset value which is a minimum distance between the first distance and the second distance. + denotes that when a value in [ ] is greater than 0, this value is taken as the loss value, and when the value in [ ] is less than 0, the loss is 0.

At step S3B, parameters of the neural network are adjusted according to the loss value. The loss value is used as a benchmark to perform BP to update the parameters of the neural network.

During actual training, a large amount of the foregoing triple sample data needs to be used, to continuously adjust the parameters of the neural network, until the loss function converges. In a process of loss transmission of the neural network, the distance between Anchor and Positive needs to be smaller, and the distance between Anchor and Negative needs to be larger, to eventually obtain a smallest interval a between the first distance and the second distance.

To improve the robustness of the neural network, data enhancement may be performed on the training data before training. A process of the data enhancement may use rotation, translation, magnification, and principal component analysis (PCA) color enhancement. Multiple fundus images using random enhancement parameters may be generated by performing data enhancement on each fundus image. For example, fundus images after data enhancement may adopt a uniform format of a 224*224 pixels and RGB color channels. During actual operations, a fundus image may first be cropped, and then subjected to data enhancement, or the fundus image may first be subjected to data enhancement, and then cropped, there is no limitation thereto.

According to a neural network training method provided in the embodiments of the present disclosure, training is performed with triple training data and a corresponding loss function, so that a distance between feature vectors extracted by a neural network from different fundus images of the same eye can be gradually decreased, and a distance between feature vectors extracted from fundus images of different eyes can be increased. After training, distances between feature vectors repeatedly extracted by the neural network from the same fundus image are small enough, and distances to feature vectors of other fundus images are large enough, that is, the information has particular uniqueness, so that feature vectors extracted by the neural network from fundus images can be used as identity information of a user.

In an optional embodiment, to further eliminate interference image information unrelated to fundus recognition and improve the recognition capability of the neural network, before training, the fundus image may first be segmented, to obtain a fundus feature image as training data.

Figure 6:
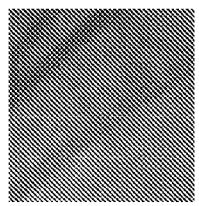
FIG. 6 shows an image patch in a fundus image.

After the fundus image is obtained, fundus features may be extracted by using a computer vision algorithm or a machine learning algorithm. For example, fundus features in the fundus image are extracted by using a segmental neural network, to obtain a probability plot or a binary image containing a fundus feature confidence level. As shown in FIG. 6, the fundus image may be divided into a plurality of image patches, the size of which is set according to the size of the fundus image. In most cases, the size of the image patch obtained after division should be significantly smaller than the size of the entire fundus image. For example, if the fundus image has a size of 1000*1000 (pixels), the size of the image patch obtained after division is 100*100 (pixels).

A blood vessel image in each image patch is segmented using a preset segmentation model to obtain segmented image patches. The segmentation model may be a neural network such as a fully convolutional network (FCN), SegNet or DeepLab. Before use, the segmentation model should be trained by the sample data to provide the segmentation model with a particular semantic segmentation capability. The training may be performed using sample image patches manually labeled with a blood vessel region.

The segmentation model extracts features of a blood vessel image in the image patch, and segments the blood vessel image into patches according to the extracted features with the blood vessel image highlighted. There are a plurality of ways for highlighting. For example, various pixel values clearly different from the background may be used to indicate positions of blood vessels or the like.

Figure 7:
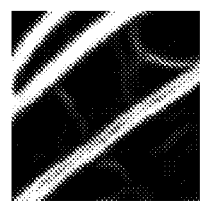
FIG. 7 shows a segmentation result of the image patch shown in FIG. 6.
Figure 8:
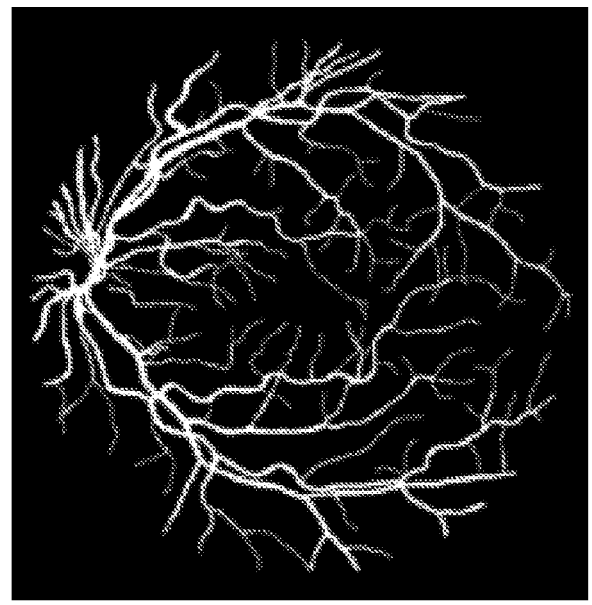
FIG. 8 shows a fundus blood vessel image.

The image patch shown in FIG. 6 is input into the segmentation model to obtain a segmented image patch shown in FIG. 7. The segmentation model used in this embodiment outputs a binary image. The binary image uses two pixel values to respectively express the background and the blood vessel image, to intuitively highlight positions of blood vessels. Segmented image patches are spliced to form a fundus blood vessel image, to obtain an image shown in FIG. 8, and then the image shown in FIG. 8 is used as training data.

In an optional embodiment, a similar method may be used to extract other features, for example: features such as the optic disc, macula, and retina. Through the extraction of fundus features, interference image information unrelated to fundus identity recognition can be greatly eliminated, thereby significantly improving the recognition performance of the model.

There may be advanced indirect features (or referred to as abstract features) in the fundus feature image, for example, positions and directions of blood vessel bifurcations, positions and directions of blood vessel intersections, and blood vessel vectograph. After an original fundus image is acquired, the foregoing indirect features may be extracted from the fundus image as training data.

Therefore, the present disclosure may use a form of hardware only embodiments, software only embodiments, or embodiments with a combination of software and hardware. Therefore, the present disclosure may use a form of hardware only embodiments, software only embodiments, or embodiments with a combination of software and hardware. Moreover, the present disclosure may use a form of a computer program product that is implemented on one or more computer-usable storage media (including but not limited to a disk memory, a compact disc read-only memory (CD-ROM), an optical memory, and the like) that include computer usable program code.

The present disclosure is described with reference to the flowcharts and/or block diagrams of the method, the device (system), and the computer program product according to the embodiments of the present disclosure. It should be understood that computer program instructions may be used to implement each process and/or each block in the flowcharts and/or the block diagrams and a combination of a process and/or a block in the flowcharts and/or the block diagrams. These computer program instructions may be provided for a general-purpose computer, a dedicated computer, an embedded processor, or a processor of any other programmable data processing device to generate a machine, so that the instructions executed by a computer or a processor of any other programmable data processing device generate an apparatus for implementing a specific function in one or more processes in the flowcharts and/or in one or more blocks in the block diagrams.

These computer program instructions may be stored in a computer readable memory that can instruct the computer or any other programmable data processing device to work in a specific manner, so that the instructions stored in the computer readable memory generate an artifact that includes an instruction apparatus. The instruction apparatus implements a specific function in one or more processes in the flowcharts and/or in one or more blocks in the block diagrams.

These computer program instructions may be loaded onto a computer or another programmable data processing device, so that a series of operations and steps are performed on the computer or the another programmable device, thereby generating computer-implemented processing. Therefore, the instructions executed on the computer or the another programmable device provide steps for implementing a specific function in one or more processes in the flowcharts and/or in one or more blocks in the block diagrams.

Obviously, the foregoing embodiments are merely examples for clear description, rather than a limitation to implementations. For a person having ordinary skills in the art, other changes or variations in different forms may also be made based on the foregoing description. All implementations cannot and do not need to be exhaustively listed herein. Obvious changes or variations that are derived there from still fall within the protection scope of the disclosure of the present disclosure.

What is claimed is:

1. A method of identity information comparison based on a fundus image, the method comprising:
   recognizing a fundus image by using a neural network to obtain a multi-dimensional feature vector representing the identity of a user;
   comparing the obtained multi-dimensional feature vector with each pre-stored multi-dimensional feature vector in a database; and
   determining, according to the comparison result, whether there is a matching between a currently obtained multi-dimensional feature vector and a multi-dimensional feature vector pre-stored in the database;
   wherein the neural network is trained using triple sample data, wherein the triple sample data comprise a first fundus image sample, a second fundus image sample, and a third fundus image sample, the second fundus image sample and the first fundus image sample are fundus images of a same person, and the third fundus image sample and the first fundus image sample are fundus images of different people;
   wherein in a process of training the neural network, the neural network separately extracts multi-dimensional feature vectors of the first fundus image sample, the second fundus image sample and the third fundus image sample, calculates a first distance between the second fundus image sample and the first fundus image sample and a second distance between the third fundus image sample and the first fundus image sample according to the three extracted multi-dimensional feature vectors, obtains a loss value according to the first distance and the second distance, and adjusts parameters of the neural network according to the loss value;
   wherein the adjusting parameters of the neural network according to the loss value comprise: feeding back the loss value to the neural network, to enable the neural network to adjust the parameters according to the loss value to decrease the first distance and increase the second distance until the first distance is smaller than the second distance by a preset value.

2. The method of claim 1, wherein the determining, according to the comparison result, whether there is a matching between a currently obtained multi-dimensional feature vector and a multi-dimensional feature vector pre-stored in the database comprises:
   calculating a distance between each pre-stored multi-dimensional feature vector and the currently obtained multi-dimensional feature vector respectively; and
   determining, according to the distance, whether each pre-stored multi-dimensional feature vector matches the currently obtained multi-dimensional feature vector.

3. The method of claim 1, wherein the fundus image comprises a left-eye fundus image and a right-eye fundus image, the database is configured to store user data, each group of user data comprises a first pre-stored multi-dimensional feature vector corresponding to a left eye and a second pre-stored multi-dimensional feature vector corresponding to a right eye, and the multi-dimensional feature vector comprises a first multi-dimensional feature vector corresponding to the left-eye fundus image and a second multi-dimensional feature vector corresponding to the right-eye fundus image.

4. The method of claim 1, wherein the fundus image comprises a left-eye fundus image and a right-eye fundus image, the database is configured to store user data, and each group of user data comprises one pre-stored multi-dimensional feature vector; and
   the obtaining a multi-dimensional feature vector representing the identity of a user comprises:
   acquiring the first multi-dimensional feature vector corresponding to the left-eye fundus image and the second multi-dimensional feature vector corresponding to the right-eye fundus image that are output by the neural network; and
   combining the first multi-dimensional feature vector and the second multi-dimensional feature vector to obtain the multi-dimensional feature vector representing the identity of the user.

5. The method of claim 1, wherein the fundus image is a left-eye fundus image or a right-eye fundus image, the database is configured to store user data, and each group of user data comprises a first pre-stored multi-dimensional feature vector corresponding to a left eye or a second pre-stored multi-dimensional feature vector corresponding to a right eye.

6. A method of identity verification based on a fundus image, the method comprising:
   acquiring a fundus image of a user; and
   determining, by using the method of claim 1, whether there is a matching between a multi-dimensional feature vector of the fundus image and a multi-dimensional feature vector matching pre-stored in a database, to complete verification of the identity of the user.

7. The method of claim 6, further comprising:
   when there is no pre-stored multi-dimensional feature vector matching a currently obtained multi-dimensional feature vector in the database, storing the currently obtained multi-dimensional feature vector in the database as identity information of the user.

8. A device of identity information comparison based on a fundus image, the device comprising: at least one processor, and a memory communicatively connected to the at least one processor, wherein the memory stores an instruction executable by one processor, which when executed by the at least one processor, causes the at least one processor to perform operations comprising:

recognizing a fundus image by using a neural network to obtain a multi-dimensional feature vector representing the identity of a user;

comparing the obtained multi-dimensional feature vector with each pre-stored multi-dimensional feature vector in a database; and determining, according to the comparison result, whether there is a matching between a currently obtained multi-dimensional feature vector and a multi-dimensional feature vector pre-stored in the database;

wherein the neural network is trained using triple sample data, wherein the triple sample data comprise a first fundus image sample, a second fundus image sample, and a third fundus image sample, the second fundus image sample and the first fundus image sample are fundus images of a same person, and the third fundus image sample and the first fundus image sample are fundus images of different people;

wherein in a process of training the neural network, the neural network separately extracts multi-dimensional feature vectors of the first fundus image sample, the second fundus image sample and the third fundus image sample, calculates a first distance between the second fundus image sample and the first fundus image sample and a second distance between the third fundus image sample and the first fundus image sample according to the three extracted multi-dimensional feature vectors, obtains a loss value according to the first distance and the second distance, and adjusts parameters of the neural network according to the loss value;

wherein the adjusting parameters of the neural network according to the loss value comprise: feeding back the loss value to the neural network, to enable the neural network to adjust the parameters according to the loss value to decrease the first distance and increase the second distance until the first distance is smaller than the second distance by a preset value.

9. The device of claim 8, wherein the determining, according to the comparison result, whether there is a prestored multi-dimensional feature vector matching a currently obtained multi-dimensional feature vector in the database comprises:

calculating a distance between each prestored multi-dimensional feature vector and the currently obtained multi-dimensional feature vector respectively; and determining, according to the distance, whether each prestored multi-dimensional feature vector matches the currently obtained multi-dimensional feature vector.

10. The device of claim 8, wherein the fundus image comprises a left-eye fundus image and a right-eye fundus image, the database is configured to store user data, each group of user data comprises a first prestored multi-dimensional feature vector corresponding to a left eye and a second prestored multi-dimensional feature vector corresponding to a right eye, and the multi-dimensional feature vector comprises a first multi-dimensional feature vector corresponding to the left-eye fundus image and a second multi-dimensional feature vector corresponding to the right-eye fundus image.

11. The device of claim 8, wherein the fundus image comprises a left-eye fundus image and a right-eye fundus image, the database is configured to store user data, and each group of user data comprises one prestored multi-dimensional feature vector; and wherein the obtaining a multi-dimensional feature vector representing the identity of a user comprises:

acquiring the first multi-dimensional feature vector corresponding to the left-eye fundus image and the second multi-dimensional feature vector corresponding to the right-eye fundus image that are output by the neural network; and combining the first multi-dimensional feature vector and the second multi-dimensional feature vector to obtain the multi-dimensional feature vector representing the identity of the user.

12. The device of claim 8, wherein the fundus image is a left-eye fundus image or a right-eye fundus image, the database is configured to store user data, and each group of user data comprises a first prestored multi-dimensional feature vector corresponding to a left eye or a second prestored multi-dimensional feature vector corresponding to a right eye.

* * * * *